(12) United States Patent
Benson et al.

(10) Patent No.: US 6,184,435 B1
(45) Date of Patent: Feb. 6, 2001

(54) TRANSGENIC MOUSE EXPRESSING APP770-V717F

(75) Inventors: Merrill D. Benson; Jill Murrell; Martin Farlow; Bernardino Ghetti, all of Indianapolis, IN (US)

(73) Assignee: Advanced Research and Technology Institute, Bloomington, IN (US)

( * ) Notice: Under 35 U.S.C. 154(b), the term of this patent shall be extended for 0 days.

(21) Appl. No.: 08/475,176

(22) Filed: Jun. 7, 1995

Related U.S. Application Data

(62) Division of application No. 08/434,018, filed on May 3, 1995, now Pat. No. 5,879,883, which is a continuation of application No. 08/176,318, filed on Jan. 3, 1994, now abandoned, which is a continuation of application No. 07/770,581, filed on Oct. 3, 1991, now abandoned.

(51) Int. Cl.$^7$ ...................... A01K 67/027; A01K 67/033; G01N 33/00

(52) U.S. Cl. .................................. 800/18; 800/3; 800/12

(58) Field of Search .................................. 800/2, DIG. 1, 800/18, 3, 12; 424/9.2; 935/60

(56) References Cited

U.S. PATENT DOCUMENTS

| | | | |
|---|---|---|---|
| 4,736,866 | 4/1988 | Leder et al. | 800/1 |
| 4,965,190 | 10/1990 | Woo et al. | 435/6 |
| 5,220,013 | 6/1993 | Ponte et al. | 536/23.5 |
| 5,234,814 | 8/1993 | Card et al. | 435/7.21 |
| 5,387,742 | 2/1995 | Cordell | 800/2 |

OTHER PUBLICATIONS

Selkoe (1991) Nature 354, 432–433.*
Science, vol. 255, pp. 1200–1202, 1992.*
Felsenstein et al (2995) Alz. Parkensons Disease, L, Hanea Ed., Plenum Press, NY. 401–409.*
Games et al (1992) Neurokio. Aging 13, 569–576.*
Podlisny et al (1992) Neurokio Aging 13, 561–567.*
Secreted amyloid B–protein similar to that in the senile plagues of Alzheimer's disease is increased in vivo by the presenilin 1 and 2 and APP mutations linked to familial Alzheimer's disease, Aug. 1996, Nature Medicine, vol. 2, No. 8, pp. 864–870.
Clinical characterisctics in a kindred with ealry–onset Alzheimer's disease and their linkage to a G–T change at position 2149 of the amyloid precursor protein gene, Nuerology 44, pp. 105–111, Jan. 1994.
Alzheimer–type neuropathology in transgenic mice overexpressing V717F B–amyloid precursor protein, Letters To Nature, vol. 373, pp. 523–527, Feb. 9, 1995.
Correlative Memory Deficits, AB Elevation, and Amyloid Plaques in Transgenic Mice, Science, vol. 274, pp. 99–102, Oct. 1996.
Transgenic Animals, Science, vol. 140, pp. 1468–1474, Jun. 1988.
Relation of Neuronal APP–755/APP–695 mRNA Ratio and Neuritic Plaque Density in Alzheimer's Disease, Science, vol. 248, pp. 854–857, May 1990.
Deposits of Amyloid B Protein in the Central Nervous System of Transgenic Mice, Science, vol. 253, pp. 323–326, Jul. 19, 1991.
Formation of B–amyloid protein deposits in brains of transgenic mice, Nature, vol. 352, pp. 239–241, Jul. 18, 1991.
Proteolytical processing of mutated human amyloid precursor protein in transgenic mice, Molecular Brain Research 47, 108–116, Feb. 1997.
Somatic Expression of herpes Thymidine Kinase in Mice following Injection of a Fusion Gene into Eggs, Cell, vol. 27, 223–31, Nov. 1981.
Introduction of a rabbit B–globin gene into the mouse germ line, Nature, vol. 294, pp. 92–94.
Factors affecting the efficiency of introducing foreign DNA into mice by microinjecting eggs, Proc. Natl. Acad. Sci. USA, vol. 82, pp. 4438–4442.
A Foreign B–Globin Gene in Tranagenic Mice Integration at Abnormal Chromosomal Positions and Expression in Inappropriate Tissues, Cell 34, pp. 343–58, 1983.
Minireview: Creating Animal Models of Genetic Disease, Am. J. Hum. Genet. 43, pp. 582–586, 1988.
Alzheimer's Disease: A Cell Biological Perspective, Science, vol. 256, pp. 780–783, May 8, 1992.
Segregation of a missense mutation in the amyloid precursor protein gene with familial Alzheimer's disease, Nature, vol. 349, pp. 704–706, Feb. 21, 1991.
PDGF B–Chain in Neurons of the Central Nervous System, Posterior Pituitary, and in a Transgenic Model, Cell, vol. 64, 217–27, Jan. 11, 1991.
Transgenic Mice Expressing Hamster Prion Protein Produce Species–Specific Scrapie Infectivity and Amyloid Plaques, Cell, vol. 59, pp. 847–857, Dec. 1, 1989.
Expression of the Human B–Amyloid Protein of Alzheimer's Disease Specifically in the Brains of Transgenic Mice, The Journal of Biological Chemistry, vol. 266, No. 32, pp. 21331–21334, Nov. 16, 1991.

* cited by examiner

*Primary Examiner*—Deborah Crouch
(74) *Attorney, Agent, or Firm*—Woodard, Emhardt, Naughton, Moriarty & McNett

(57) ABSTRACT

Methods for screening for risk of Alzheimer's disease involve assaying for a guanine to thymine substitution at position 1924 of the gene encoding the human amyloid precursor protein. Also described are transgenic non-human mammals, especially transgenic mice, harboring an expressable gene sequence encoding human amyloid precursor protein having a phenylalanine for valine amino acid substitution in the transmembrane domain of the amyloid precursor protein.

2 Claims, 4 Drawing Sheets ccaaatgtccccgtcatttaagaaatgaaattcttctaattgcgtttataaattgta aattatattgcatttagaaattaaaattctttttcttaatttgttttcaag GTG TTC
                                                     Val Phe
                                                     1840
                                                      ↕
                                                     614

TTT GCA GAA GAT GTG GGT TCA AAC AAA GGT GCA ATC ATT GGA CTC
Phe Ala Glu Asp Val Gly Ser Asn Lys Gly Ala Ile Ile Gly Leu

▼         T
ATG GTG GGC GGT GTT GTC ATA GCG ACA GTG ATC GTC ATC ACC TTG
Met Val Gly Gly Val Val Ile Ala Thr Val Ile Val Ile Thr Leu
                                         Phe

GTG ATG CTG AAG AAG AAA CAG TAC ACA TCC ATT CAT CAT GGT GTG
Val Met Leu Lys Lys Lys Gln Tyr Thr Ser Ile His His Gly Val

1986
 ↕
GTG GAG gtaggtaaacttgactgcatgtttccaagtgggaattaagactatgagag
Val Glu
    669

*Fig. 1*

TRANSGENIC MOUSE EXPRESSING APP770-V717F

The present application is a divisional of Ser. No. 08/434,018 filed May 3, 1995, which is a continuation of Ser. No. 08/176,318 filed Jan. 3, 1994, now abandoned, which is a continuation of Ser. No. 07/770,581 filed Oct. 3, 1991, now abandoned.

BACKGROUND OF THE INVENTION

The present invention relates to a method for screening for risk of Alzheimer's disease in a patient, and to a transgenic mammal carrying a mutated human gene associated with the development of Alzheimer's disease.

Alzheimer's disease is a form of localized amyloidosis characterized by cerebral cortical amyloid plaques, neurofibrillary tangles, and amyloid deposits within the walls of leptomeningeal vessels. Although most cases of Alzheimer's disease are sporadic, kindreds with autosomal dominant inheritance of the syndrome suggest that a single mutation may be important in pathogenesis.

Hereditary or familial Alzheimer's disease is an autosomal dominant form of localized amyloidosis. Patients with hereditary Alzheimer's disease typically develop three pathologic lesions: (i) senile plaques in the cerebral cortex characterized by a central amyloid core surrounded by dystrophic neurites; (ii) neurofibrillary tangles; and (iii) congophilic angiopathy of the leptomeningeal vessels. The amyloid deposits in the senile plaques and in the blood vessel walls contain a fibril subunit protein of 39 to 43 amino acid residues [See, G. G. Glenner and C. W. Wong, *Biochem. Biophys., Res. Commun.*, 120, p. 885 (1984)], which is a portion of the carboxyl terminus of the amyloid precursor protein (APP). Sequence analysis of cDNA clones of APP has shown that there are multiple forms of mRNA which are the result of alternate splicing of a transcript from a single gene. See, J. Kang et al., *Nature*, 325, p. 733 (1987); P. Ponte et al., Ibid, 331, p. 525 (1988); R. E. Tanzi et al., Ibid, p. 528; N. Kitaguchi, Y. Takahashi, Y. Tokushima, S. Shiojiri, H. Ito, Ibid, p. 530; N. Kitaguchi et al., *Biochim. Biophys. Acta*, 1039, p. 105 (1990); and S. Yoshikai, H. Sasaki, K. Doh-ura, H. Furuya, Y. Sasaki, *Gene* 87, p. 257 (1990). Although the sequence of the APP gene from some patients with either sporadic or familial Alzheimer's disease is normal [See, D. Goldgaber, M. I. Lerman, O. W. McBridde, U. Saffotti, D. C. Gajdusek, *Science* 235, p. 887 (1987); R. E. Tanzi et al., ibid, p. 880; N. K. Robakis, N. Ramakrishna, G. Wolfe, H. M. Wisniewski, *Proc. Natl. Acad. Sci. U.S.A.*, 84, p. 4190 (1987); H. G. Lemaire et al., *Nucleic Acids. Res.* 17, p. 51 (1989); and M. P. Vitek et al., Mol. *Brain Res.* 4, p. 121 (1988)], a cytosine to thymine missense mutation in the membrane-spanning domain of the APP gene (causing a valine to isoleucine change in the corresponding amino acid sequence of the encoded APP) has been identified in patients from several families with familial Alzheimer's disease. See, A. Goate et al., *Nature* 349, p. 704 (1991).

SUMMARY OF THE INVENTION

In the applicants' work, analysis of DNA from a family with autopsy-proven Alzheimer's disease revealed a single amino acid substitution (phenylalanine for valine) in the transmembrane domain of the amyloid precursor protein. This substitution is caused by a point mutation at nucleotide position 1924 (using the APP695 transcript) of the gene encoding the amyloid precursor protein in which guanine (normal) is replaced by thymine (mutant). This mutation correlated with the presence of Alzheimer's disease in all studied patients. Accordingly, one embodiment of the invention relates to a method for screening for risk of Alzheimer's disease in a patient. The method includes the step of assaying for a guanine to thymine point mutation at position 1924 of the patient's gene encoding the amyloid precursor protein.

The applicants' discovery also provides access to transgenic non-human mammals, preferably rodents such as mice, harboring an expressable gene sequence encoding human amyloid precursor protein having a phenylalanine for valine amino acid substitution in the transmembrane domain of the amyloid precursor protein. Access is also provided to vectors containing the above-noted gene sequence which can be used to create transgenics for study or protein expression (i.e. for production and recovery), and to the above-noted mutant amyloid precursor protein( with the phenylalanine for valine substitution) in substantially pure form.

Additional objects, advantages and embodiments of the invention will be apparent from the following description and appended claims.

BRIEF DESCRIPTION OF THE FIGURES

FIG. 1 sets forth the DNA sequence of a region amplified by PCR (nucleotides 1732 through 2036). Lower case letters designate introns; capital letters designate exon 15, which encodes the C-terminal portion of amyloid β-protein, amino acids 614 through 669 (exon 17 if numbered by the APP770 transcript. Solid lines indicate oligonucleotide primers used in the PCR reactions. The mutation at position 1924 is in the box. Solid arrowhead indicates the carboxyl terminus of the longest β-amyloid peptide sequence that has been reported (43 residues).

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

Genomic DNA from three generations of a family with classic early-onset autosomal dominant Alzheimer's disease was used in applicants' study. In particular, exon 15 of the APP gene was amplified and sequenced using the polymerase chain reaction (PCR). See, e.g., H. G. Lemaire et a., *Nucleic Acids Res.* 17, p. 51 (1989); A. Goate et al. *Nature* 349, p. 704 (1991); and U. B. Gyllenstein and H. A. Erlich, *Proc. Natl. Acad. Sci. U.S.A.* 85, p. 7652 (1988). The DNA sequence of a region amplified by PCR is set forth in FIG. 1.

Figure 2:
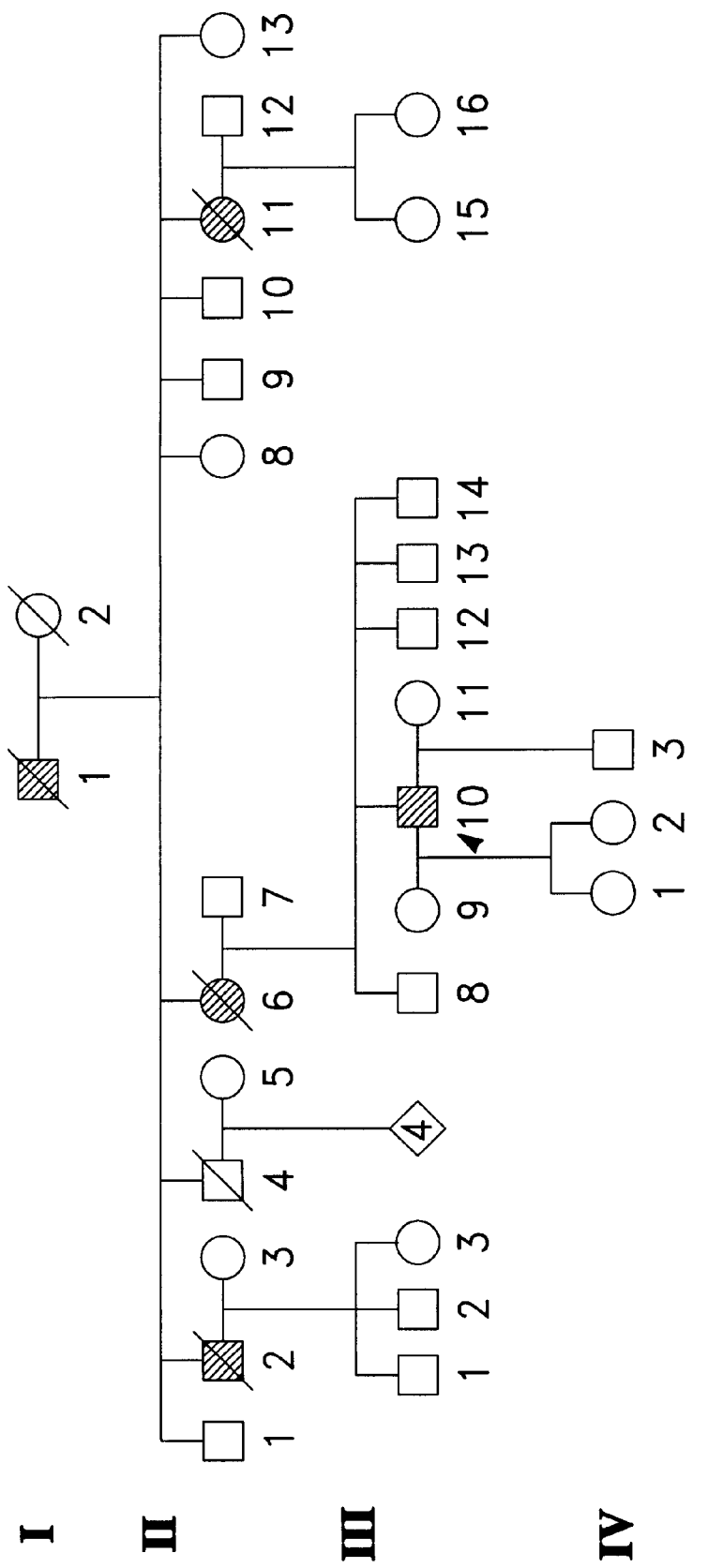
FIG. 2 sets forth an abbreviated pedigree of a family with early onset Alzheimer's disease used in applicants' study. Solid symbols indicate affected individuals. Tissue DNA was studied from all affected individuals in generation II. DNA isolated from peripheral blood leukocytes of III-10 and the five unaffected individuals of generation II was studied. Arrow denotes propositus.
Figure 3:
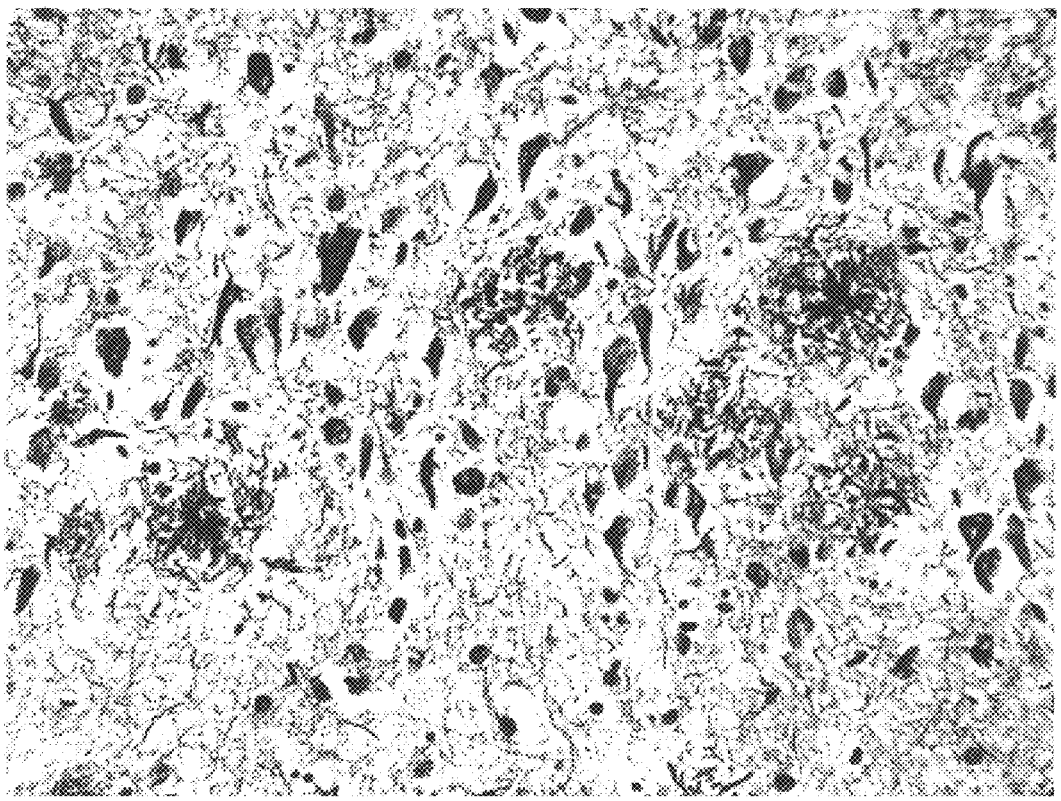
FIG. 3 depicts a stained preparation showing neurofibrillary tangles and senile plaques in the subiculum of patient II-11 of the FIG. 2 pedigree. In the plaques both a neuritic crown and a prominent amyloid core are seen. The majority of nerve cells contain neurofibrillary tangles. Preparation was stained with DeMyer modification of Hortega silver carbonate method; 250× magnification.

An abbreviated pedigree of the family of the applicants' study is set forth in FIG. 2. Affected members of this family (solid symbols in FIG. 2) show clinical onset of disease with short-term memory problems in their 40's. Other cognitive difficulties develop as the disease gradually progresses. Disease duration is typically 7 years. Postmortem examinations of the brains of three members of generation II (see FIG. 2) showed histologic lesions typical of Alzheimer's disease with only minor vascular amyloid deposits and no evidence of cerebral hemorrhage. See FIG. 3. Individuals II-2, II-6 and II-11 developed dementia at ages 41, 42 and 45 and died at ages 49, 48, and 53, respectively. One individual in generation III is presently 44years of age and suffers from a severe presenile dementia. DNA from the five unaffected members of generation II, who are well beyond the age of expression of disease in this kindred, was also analyzed. As indicated above, in the affected members, the applicants' analysis revealed a point mutation at nucleotide position 1924 of the gene encoding the amyloid precursor protein in which guanine is replaced by thymine. This mutation causes an amino acid substitution (phenylalanine for valine) in the transmembrane domain of the amyloid precursor protein, specifically at amino acid 717 (transcript $APP_{770}$), which is two residues down from the carboxy terminus of the β-amyloid peptide (See FIG. 1).

In contrast to linkage analyses that do not show association of Alzheimer's disease with the APP gene [See, R. E. Tanzi et a., *Nature* 329 p. 156 (1987); C. V. Broeckhoven et al., ibid, p. 153; and G. D. Schellenberg et al., *Am. F. Hum Genet.* 48, p. 563 (1991)], the occurance of the mutation in the APP in individuals from two generations of a kindred affected with Alzheimer's disease is evidence for this mutation as the cause of amyloid deposition and dementia. This mutation is consistent with observations of familial amyloidotic polyneuropathy (FAP), in which multiple single amino acid substitutions are associated with amyloid fibril formation. See, M. D. Benson and M. R. Wallace, in *The Metabol. Basis of Inherited Disease*, C. R. Scriver, A. L. Beaudet, W. S. Sly and D. Valle, Eds. (McGraw Hill, ed VI, New York, 1989, p. 2439. Although the pathogenesis of disease in systemic amyloidosis is generally considered to involve the formation of amyloid deposits that lead to destruction of normal tissue, similar conclusions cannot yet be drawn for hereditary Alzheimer's disease. Although the applicants' invention is not bound by any theory, the dementia may be in part the result of altered function of the variant APP protein and not the direct result of displacement of normal tissue by amyloid fibrils.

As indicated, the Val to Phe amino acid substitution is two residues beyond the carboxyl terminus of the β-amyloid peptide subunit isolated from fibrils. Single amino acid substitutions are also found in other forms of hereditary amyloidosis. In the transthyretin amyloidoses (FAP, types I and II), a number of single amino acid substitutions in transthyretin are associated with the amyloid syndrome. See, M. D. Benson and M. R. Wallace, in *The Metabol. Basis of Inherited Disease*, C. R. Scriver, A. L. Beaudet, W. S. Sly and D. Valle, Eds. (McGraw Hill, ed VI, New York, 1989, p. 2439. Similarly, FAP type III is associated with amyloid deposits that contain a peptide of apolipoprotein Al with a single amino acid substitution (Gly to Arg). See, W. C. Nichols, R. E. Gregg, H. B. Brewer, Jr., M. D. Benson, *Genomics* 8, p. 318 (1990). In Gerstmann-Straussler-Scheinker disease (GSS), a hereditary adult-onset dementia with cerebral amyloid plaques composed of a fragment of the prion protein, every GSS family studied to date has a mutation in the gene coding for this protein. See, K. Doh-ura, J. Tateiski, H. Sasaki, T. Kitamoto, Y. Sakaki, *Biochem. Biophys. Res. Commun.*, 163, p. 97 (1989); K. Hsiao et al., *Nature*, 338, p. 342 (1989); and F. Tagliavini et al., *EMBO J.*, 1, p. 513 (1991). Hereditary cerebral hemorrhage with amyloidosis in Icelandic kindreds (HCHWA-I) is associated with a single amino acid substitution in cystatin C [See, J. Ghiso, O. Jensson, B. Fragione, *Proc. Natl. Acad. Sci. U.S.A.*, 83, p. 2974 (1986)], and a similar syndrome in Dutch kindreds (HCHWA-D) is associated with a single amino acid substitution of Gln for Glu in APP. See, E. Levy, et. al., *J. Exp. Med.* 169, p. 1771 (1989).

As to assaying for the above-mentioned guanine to thymine point mutation, many methods for detecting single base changes in genomic DNA are known and will be suitable for the methods of the present invention. For example, the technique applied need not be direct DNA sequencing, but rather can include an analysis of other materials derived from or caused by the point mutation. For instance, methods of detecting single base changes in genomic DNA which are more readily applied than direct DNA sequencing are preferred. As one example, the applicants have employed the PCR-IMRA technique as further detailed in Example 2 below. In any event, the utilization of these and other known techniques in the present invention is within the skill of artisans in the field. Further, genomic DNA can be isolated from any suitable source in the patient (e.g. tissues, blood leukocytes, etc.), and the methods of the invention applied to any individual to be screened, including in prenatal screening procedures.

As indicated above, a further embodiment of the invention relates to a transgenic, non-human mammal, preferably a rodent such as a mouse, harboring an expressable gene sequence encoding human amyloid precursor protein having a phenylalanine for valine amino acid substitution (at amino acid 717, $APP_{770}$ transcript) in the transmembrane domain of the amyloid precursor protein. The gene sequence is introduced, e.g. through an appropriate vector, into the mammal or an ancestor of the mammal at an embryonic stage, preferably at the single-cell stage (i.e. fertilized eggs). The resulting transgenic animal harbors the expressable mutated gene in its somatic and germ cells and may be used in further study of CNS amyloidosis and the effects of the point mutation and potential development of Alzheimer's disease and/or its related symptoms. The creation of transgenics and the related methodologies are well known [see, e.g. U.S. Pat. No. 4,736,866] and in particular have also been applied to create transgenic rodents expressing normal human APP protein. See, D. O. Wirak et al., "Deposits of Amyloid β Protein in the Central Nervous System of Transgenic Mice,", *Science*, 253, pp. 323–325 (1991); and, D. Quon et al., "Formation of β-amyloid Protein Deposits in Brains of Transgenic Mice,", *Nature*, 352, pp.239–241 (1991). These techniques are readily applied in the present invention.

The following examples are illustrative, and not restrictive, of the invention. All publications cited herein are hereby incorporated by reference in their entirety.

EXAMPLE 1

Direct DNA Sequencing

Genomic DNA was isolated from tissue specimens or peripheral blood leukocytes. Liver tissue of subjects II-11 had been frozen at the time of autopsy in 1980. Brain tissue from subject II-6 had been fixed in formalin in 1968. For DNA extraction, the cerebelum was used because of the high density of cells. For subject II-2, DNA was extracted from a Congo red-stained histologic section of cerebral cortex. See, W. C. Nichols, R. E. Gregg, H. B. Brewer, M. G. Benson, Genomics, 8, p. 318 (1990).

Figure 4A:
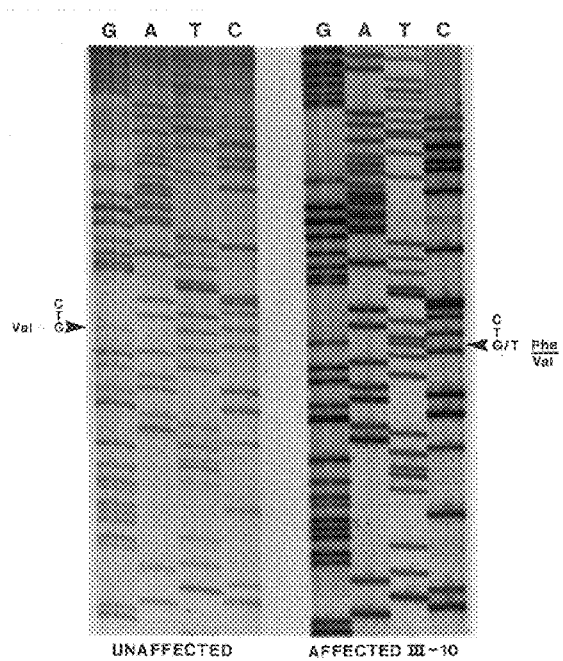
FIG. 4 sets forth autoradiographs of sequencing gels of the APP gene exon 15 in affected and unaffected individuals. (A) Positive strand sequence of DNA from peripheral blood. (B) Sequences from formalin fixed brain tissues. Sequencing of the opposite strand confirmed the mutation. Numbering is according to the APP695 transcript.
Figure 4B:
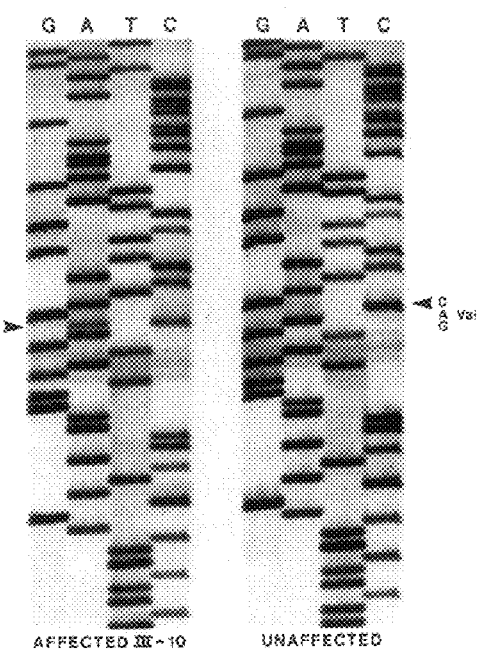

Direct sequencing of PCR-amplified DNA of patient III-10 showed both a guanine and thymine at position 1924 of APP (see FIG. 4). Thus, the individual was heterozygous with both a normal GTC (valine) and a variant TTC (phenylalanine) condon. Direct sequencing of amplified tissue DNA from the three affected members in generation II showed that each was heterozygous for the point mutation at position 1924. Direct DNA sequencing for the five unaffected generation II siblings who are beyond the usual age of onset of disease revealed only the normal guanine at position 1924. In addition, analysis of DNA from 100 unrelated individuals failed to show this mutation, which suggests this is not a polymorphism that co-segregates with disease by chance.

EXAMPLE 2

Non-Isotopic DNA Test

Total genomic DNA was isolated from either peripheral blood leukocytes when possible [See, D. Goldgaber, M. I. Lerman, O. W. McBridde, U. Saffotti, D. C. Gajdusek, Science 235, p. 887 (1987); R. E. Tanzi et al., ibid, p. 880; N. K. Robakis, N. Ramakrishna, G. Wolfe, H. M. Wisniewski, Prod. Natl. Acad. Sci. U.S.A., 84, p. 4190 (1987)] or formalin fixed tissue sections [See, H. G. Lemaire et al., Nucleic Acids Res. 7, p. 51 (1989)], as described previously, from several generations of the family with classical early-onset familial Alzheimer's disease. Enzymatic amplification was performed in 50 μM each dNTP (Pharmacia), 0.25 U Amplitaq DNA polymerase (Perkin-Elmer Cetus), 0.5 μh DNA and 150 ng each primers APPEX15-3' and ALZ PCR-IMRA (Table 1). Primer APPEX15-3' anneals to a region near the 3+ end of exon 15 of the amyloid β-protein (exon 17 if numbered by the APP770 transcript). Primer ALZ PCR-IMRA was designed to anneal immediately 5' to the site of the G-T mutation site and contains a single mismatch near its 3' end. Amplification of the variant allele with these primers produces a Bgl II site (AGATCT) in the resulting 90 base pair PCR product, while the PCR product derived from the normal allele using the same set of primers contains no Bgl II site (FIG. 1). Amplification was performed using a Perkin-Elmer Thermal Cycler for 35 cycles consisting of denaturing at 94° for 1 minute, primer annealing at 62° for 1 minute and extending at 72° for 1 minute. Following amplification, the reactions were extracted with 100 μl Sevag and a 10 μl aliquot was electrophoresed on a 4% composite (3% FMC NuSieve/1% Bethesda Research Labs) agarose gel for 1 hour at 80 V, stained with 1 μg/ml ethidium bromide and photographed on a UV light source to ensure successful amplification. An additional 10 μl aliquot of reactions containing a predominant band of the expected size (90 bp) was digested with 14 U Bgl II (United States Biochemicals) in 1× supplied HIGH buffer at 37°. After at least 1 hour of digestion, the entire digest was electrophoresed on a 4% composite agarose gel at 80 V for 90 minutes.

Results

Testing was performed on DNA isolated from 4 family members known to be heterozygous for the variant allele by direct genomic sequencing and an additional 4 family members shown to be homozygous for the normal allele. DNA from 2 of the positive controls was obtained from formalin fixed brain tissue. DNA from the remainder of the positive controls and all 4 negative controls was isolated from peripheral blood leukocytes. Amplification of all 8 samples yielded a single predominant PCR product of the appropriate size. Digestion of the resulting PCR products revealed an additional 68 bp digestion product in all 4 positive controls, while none of the negative controls showed any evidence of an additional product. Thus, the PCR-IMRA technique can be effectively used to screen for the subject point mutation.

EXAMPLE 3

Transgenic Mammal

The method of D. O. Wirak et al., Science, 253, pp. 323–325, is used to generate a fragment containing the above-identified mutant APP gene having a guanine to thymine point mutation at position 1924. Accordingly, an open reading frame including the mutant APP is contained within a Bgl II-Bam HI restriction fragment and generated by site directed mutagenesis [L. Kunkel et al., Methods Enzymol., 154, 367 (1987)] of APP cDNA sequences with a synthetic oligonucleotide primer (5'-GGTGTTGTCATAGCGTAGGATCCGTCATCACCTTGG TG-3'). This Bgl II-Bam HI restriction fragment is ligated into the Bam HI site of pMTI-2307 [D. O. Wirak et al., EMBO J., 10, 289 (1991)] to generate inventive fragment 1 ("IF1"). An –2-kb Bam HI restriction fragment, containing APP 695 3'-end CDNA sequences, is inserted into the Bam HI site of IF1 to generate IF2. An 0.6-kb Sph I restriction fragment of pMTI-2304, containing SV40 RNA splicing signals [H. Okavama and P. Berg, Mol. Cell. Bull., 3, 280 (1983)] and SV40 viral DNA is ligated into a Sph 1 site of IF2 to generate IF3. A Not I restriction fragment of IF3 is used (in the method of D. O . Wirak et al., EMBO J., supra) to produce a transgenic mouse. This mouse thus harbors an expressable gene sequence encoding a mutant human amyloid precursor protein which has a valine to phenylalanine amino acid substitution at amino acid position 717 (transcript $APP_{770}$) in the transmembrane domain of the amyloid precursor protein.

While the invention has been described in detail in the Figures and foregoing description, the same is to be considered as illustrative and not restrictive in character, it being understood that only the preferred embodiment has been described and that all changes and modifications that come within the spirit of the invention are desired to be protected.

What is claimed is:

1. A transgenic mouse whose genome comprises a DNA sequence encoding a human amyloid precursor protein which contains a valine to phenylalanine substitution at amino acid position 717 operably linked to a promoter, and wherein expression of the DNA sequence results in detectable levels of the amyloid protein in the brain of the mouse.

2. The mouse of claim 1, wherein the valine to phenylalanine substitution is caused by a guanine to thymine substitution at position 1924 of the DNA sequence.

* * * * *

SEQUENCE LISTING (1) GENERAL INFORMATION:

(iii) NUMBER OF SEQUENCES:   1

(2) INFORMATION FOR SEQ ID NO: 1:

(i) SEQUENCE CHARACTERISTICS:
      (A) LENGTH:   305 base pairs
      (B) TYPE:     Nucleic Acid
      (C) STRANDEDNESS: Single
      (D) TOPOLOGY: Linear (ii) MOLECULE TYPE: Genomic DNA (xi) SEQUENCE DESCRIPTION:   SEQ ID NO:1:

```
CCAAATGTCC  CCGTCATTTA  AGAAATGAAA  TTCTTCTAAT  TGCGTTTATA              50

AATTGTAAAT  TATATTGCAT  TTAGAAATTA  AAATTCTTTT  TCTTAATTTG             100

TTTTCAAG GTG TTC TTT GCA GAA GAT GTG GGT TCA AAC AAA GGT              144
         Val Phe Phe Ala Glu Asp Val Gly Ser Asn Lys Gly
          1           5                      10

GCA ATC ATT GGA CTC ATG GTG GGC GGT GTT GTC ATA GCG ACA GTG           189
Ala Ile Ile Gly Leu Met Val Gly Gly Val Val Ile Ala Thr Val
         15                  20                  25

ATC TTC ATC ACC TTG GTG ATG CTG AAG AAG AAA CAG TAC ACA TCC           234
Ile Phe Ile Thr Leu Val Met Leu Lys Lys Lys Gln Tyr Thr Ser
     30                  35                  40

ATT CAT CAT GGT GTG GTG GAG GTAGGTAAAC TTGACTGCAT                     275
Ile His His Gly Val Val Glu
             45

GTTTCCAAGT  GGGAATTAAG  ACTATGAGAG                                    305
```